US00PP32041P2

(12) United States Plant Patent
Hansen

(10) Patent No.: US PP32,041 P2
(45) Date of Patent: Aug. 4, 2020

(54) **X *MANGAVE* PLANT NAMED 'PINEAPPLE PUNCH'**

(50) Latin Name: **X *mangave***
Varietal Denomination: Pineapple Punch

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,654

(22) Filed: Nov. 15, 2019

(51) Int. Cl.
*A01H 5/00* (2018.01)
*A01H 6/12* (2018.01)

(52) U.S. Cl.
USPC ..... Plt./373

(58) Field of Classification Search
USPC ..... Plt./373
CPC ..... A01H 5/00; A01H 6/12
See application file for complete search history.

*Primary Examiner* — Annette H Para

(57) ABSTRACT

A new and distinct x *Mangave* plant named 'Pineapple Punch' characterized by moderate to rapid growth rate and compact habit of stiff, upright to outward pointing, succulent foliage gray-green coloring and burgundy speckling in the leaf centers and cherry red in the margins. The leaves have a yellowish margin that varies from chartreuse to bright gold.

1 Drawing Sheet

Botanical classification: x *Mangave*.
Variety denomination: 'Pineapple Punch'.

STATEMENT REGARDING PRIOR DISCLOSURES UNDER 37 CFR 1.77(b)(6)

No plants of x *Mangave* 'Pineapple Punch' have been sold, by this name or any other name, in this country or anywhere in the world, nor has any disclosure of the new plant been made prior the filing date of this application.

BACKGROUND OF THE INVENTION

The present invention relates to the new and distinct X *Mangave* plant, X *Mangave* 'Pineapple Punch' discovered by the inventor at a wholesale perennial nursery in Zeeland, Mich., USA as a single, individual, whole-plant mutation in a tissue culture batch of x *Mangave* 'Pineapple Express' U.S. Plant Pat. No. 28,613. The mutation was found on Oct. 17, 2017. Through repeated trials beginning in 2018 at the same nursery the new plant was referred to by the breeder code 18-SP-MANG-751. The new plant has been successfully asexually propagated by division at the same nursery in Zeeland, Mich. Asexually propagated divisions have been found to produce stable and identical plants that maintain all the unique characteristics of the original plant.

BRIEF SUMMARY OF THE INVENTION

X *Mangave* 'Pineapple Punch' differs from its parents as well as all other *Manfreda, Agave* and x *Mangave* known to the applicant. Compared to the mutation parent, x *Mangave* 'Pineapple Express', the new plant has creamy yellow margins on the foliage but is very similar in habit and size. The most similar known X *Mangave* cultivars are 'Navajo Princess' U.S. Plant patent application Ser. No. No. 16/350,481, 'Snow Leopard' U.S. Plant patent application Ser. No. 16/501,208, 'Carnival' U.S. Plant patent application Ser. No.

16/501,028 and 'Kaleidoscope' U.S. Plant Pat. No. 28,614. 'Navajo Princess' has more arching habit with broader, longer, more folded foliage that has margins of more creamy white. 'Snow Leopard' has fewer, longer and broader leaves with a lighter, creamy-white margin and a more arching habit. 'Carnival' has reverse variegation pattern with the darker color on the margin and the center of yellowish-green to yellowish-cream, and the foliage is broader, longer and more arching foliage with more spotting of greyed-purple to cherry red. 'Kaleidoscope' has broader, longer and more arching foliage with more spotting or greyed-purple to cherry red.

The new plant, 'Pineapple Punch', is unique from all of these *Agave, Manfreda* and X *Mangave* known to the inventor by the following combined traits:

1. Stiff, upright to outward pointing, succulent foliage with compact habit;
2. Gray-green leaves with large speckling of burgundy in the leaf center and cherry red on the margin;
3. Moderate to rapid growth rate with good natural pup production;
4. Foliage has medium width yellowish bands along the margins.

BRIEF DESCRIPTION OF THE DRAWINGS

The drawings of the new plant demonstrates the overall appearance of the new plant including the unique traits as a two-year old plant grown in a container in a greenhouse with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
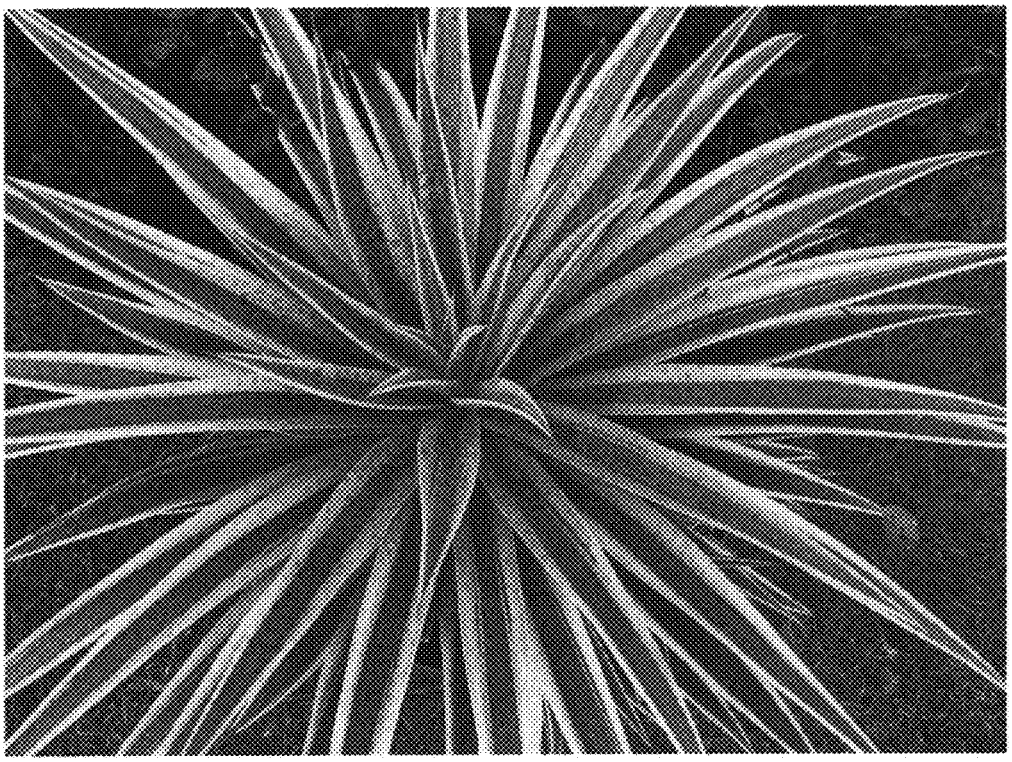
FIG. 1 shows the new plant from top view.
Figure 2:
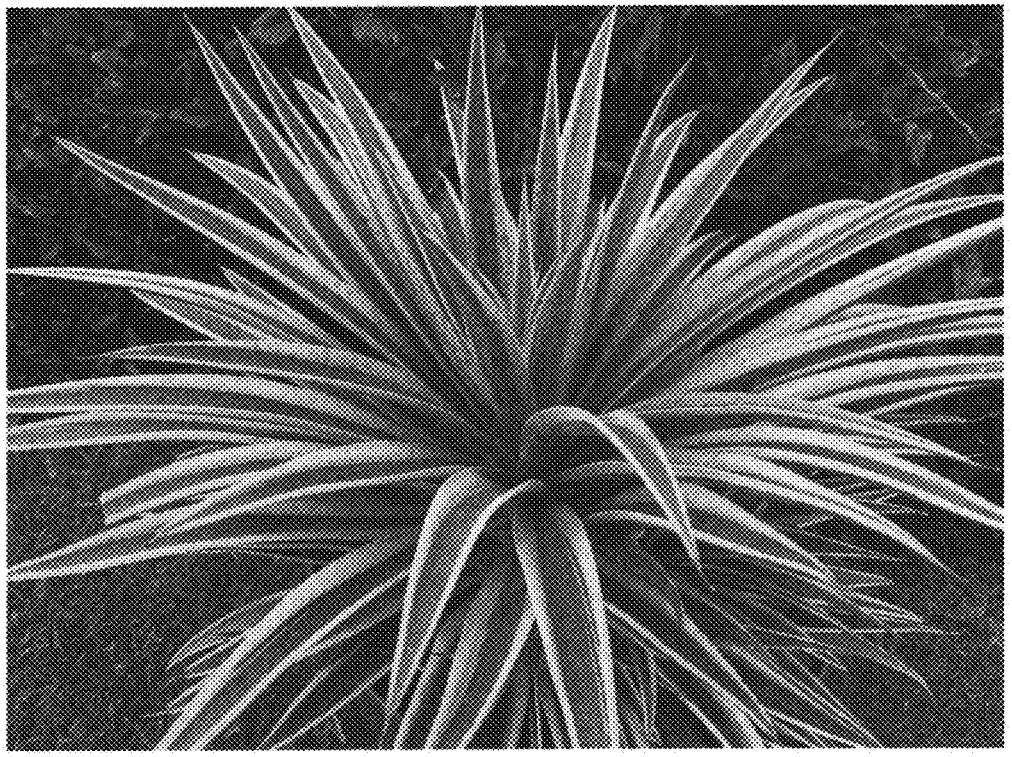
FIG. 2 shows the new plant from a side view.

The following descriptions and color references are based on the 2015 edition of The Royal Horticultural Society Colour Chart except where common dictionary terms are used. The new plant, X *Mangave* 'Pineapple Punch', has not been observed under all possible environments. The phenotype may vary slightly with different environmental conditions, such as temperature, light, fertility, moisture and maturity levels, but without any change in the genotype. The following observations and size descriptions are of a two-year-old plant in a commercial wholesale greenhouse in Zeeland, Mich. with supplemental water and fertilizer as needed.

Botanical classification: x *Mangave;*

Variety denomination: 'Pineapple Punch';

Parentage: Mutation parent x *Mangave* 'Pineapple Express';

Propagation: Division;

Time to initiate roots from division: About 21 days; time to finish in a 3.8 liter container from division: about 4 months;

Growth rate: Moderate to rapid;

Rooting habit: Fleshy, lightly branching, with roots up to 20 cm long;

Root color: Nearest RHS 158C;

Plant shape and habit: Succulent herbaceous polycarpic perennial with basal rosettes of about 100 fleshy leaves radially emerging from central rhizome, producing a symmetrical rounded mound;

Plant size: Foliage height about 42.0 cm tall from soil line to the top of the leaves and about 62.0 cm wide at the widest point at soil line; stem short, covered with leaves, about 6 cm diameter;

Foliage description: Gladiate; simple, sarcous, glabrous; glaucous; margins finely dentate with flexible teeth; apex acute with mucro; base truncate, sessile, clasping;

Number of leaves: About 100 per plant;

Leaf blades: Finely dentate; to about 33.0 cm long, about 4.0 cm wide near middle and 5.0 mm thick, average about 31.0 cm long, 3.5 cm wide and 4.5 mm thick; typically bi-laterally symmetrical; glabrous and glaucous adaxial and abaxial; with irregular speckles intensified with higher ultra violet light of between about 1.0 diameter to about 6.0 mm across and about 10.0 mm long; lighter yellowish margin to about 14.0 mm wide near middle of leaf;

Foliage fragrance: None observed;

Leaf blade color:

*Adaxial* (*young*).—Leaf center nearest RHS N138C with irregular speckles nearest RHS 146A or with a undertone of nearest a blend between RHS NN137B and RHS 187B; leaf margin nearest RHS 11C distally and RHS N144D proximally, with speckles of nearest RHS 186A.

*Abaxial* (*young*).—Leaf center nearest RHS N138D with irregular speckles nearest RHS speckles nearest a blend between RHS 137A and RHS N187B; leaf margin nearest RHS 11C distally and RHS N144D proximally, with speckles nearest RHS 186A.

*Adaxial* (*mature*).—Center variable with different light intensities or exposures, nearest a blend between RHS NN137C and RHS N138A and nearest RNS NN137C, with speckles nearest blend between RHS NN137C and RHS 187A; margin variable with light intensity or exposures, proximally nearest a blend between RHS 145A and RHS 146D, distally as bright as a blend between RHS 153D and RHS 11B and a light blush of nearest RHS 39B, with variable speckles between RHS 39B and RHS N187B.

*Abaxial* (*mature*).—Center variable nearest RHS 137B to nearest RHS N138B with speckles absent in lowest leaves to between RHS 187A and RHS N187B; margin variable, proximally nearest a blend between RHS 145A and RHS 146D, distally as bright as a blend between RHS 153D and RHS 11B and a light blush of nearest RHS 39B, with variable speckles when present between RHS 39B and RHS N187B.

*Mucro.*—Semi-flexible; straight, about 5.0 mm long.

Mucro color: Between RHS 166A and RHS 183A;

Spine texture: Semi-flexible, glabrous, sharply-pointed;

Petiole: Sessile;

Veins: Parallel; not distinct;

Flower and fruit description: Not yet observed;

Disease resistance and growth requirements: x *Mangave* 'Pineapple Punch' has not been observed to be resistant to diseases common to other x *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental x *Mangave* plant named 'Pineapple Punch' as herein described and illustrated, suitable as a potted plant or for the garden.

* * * * *